(12) United States Patent
Strohbach et al.

(10) Patent No.: US 6,686,356 B2
(45) Date of Patent: Feb. 3, 2004

(54) PYRIDOQUINOXALINE ANTIVIRALS

(75) Inventors: Joseph Walter Strohbach, Mendon, MI (US); Steven P. Tanis, Kalamazoo, MI (US); Malcolm Wilson Moon, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/325,248

(22) Filed: Dec. 19, 2002

(65) Prior Publication Data

US 2003/0130255 A1 Jul. 10, 2003

Related U.S. Application Data

(60) Provisional application No. 60/342,874, filed on Dec. 20, 2001.

(51) Int. Cl.[7] .................... A61K 31/5377; A61P 31/22; C07D 47/06
(52) U.S. Cl. ...................................... 514/233.2; 544/115
(58) Field of Search ........................ 544/115; 514/233.2

(56) References Cited

U.S. PATENT DOCUMENTS 5,792,774 A    8/1998    Haughan et al.

FOREIGN PATENT DOCUMENTS

| JP | 55049379 | 4/1980 |
| WO | WO0125239 | 4/2001 |
| WO | WO02/04445 | 1/2002 |
| WO | WO2002/00445 | * 2/2002 |

* cited by examiner

*Primary Examiner*—Robert W. Ramsuer
(74) *Attorney, Agent, or Firm*—Lucy X. Yang

(57) ABSTRACT

The present invention provides a compound of formula I

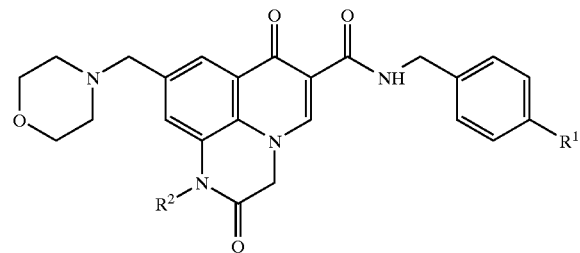

or a pharmaceutically acceptable salt thereof wherein $R^1$ and $R^2$ are as defined in the specification. The compounds are useful for the treatment of viral infections.

25 Claims, No Drawings

PYRIDOQUINOXALINE ANTIVIRALS

CROSS-REFERENCE TO RELATED APPLICATIONS

This application claims the benefit of U.S. provisional application Ser. No. 60/342,874, filed on Dec. 20, 2001, under 35 USC 119(e)(i), incorporated herein by reference in its entirety.

FIELD OF THE INVENTION

The present invention provides pyridoquinoxalines that are useful as antiviral agents. More specifically, it provides compounds of formula I described herein below against herpesviruses.

BACKGROUND OF THE INVENTION

The herpesviruses comprise a large family of double stranded DNA viruses.

They are also a source of the most common viral illnesses in man. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpesviruses 6, 7, and 8 (HHV-6, HHV-7, and HHV-8), have been shown to infect humans.

HSV-1 and HSV-2 cause herpetic lesions on the lips and genitals, respectively.

They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

The compounds of the present invention may also be useful for the treatment of herpesvirus infections in animals, for example illnesses caused by bovine herpesvirus 1–5 (BHV), ovine herpesvirus 1 and 2, Canine herpesvirus 1, equine herpesvirus 1–8 (EHV), feline herpesvirus 1 (FHV), and pseudorabies virus (PRV) viral infections.

It has been surprisingly discovered that when a $C_{1-6}$alkyl is placed on the nitrogen of the pyridoquinoxaline moiety of formula I, compounds of the present invention demonstrate greatly enhanced oral bioavailability and improved selectivity for the viral targets.

INFORMATION DISCLOSURE

U.S. Pat. No. 5,792,774 discloses specific quinoline derivatives that are alleged to have therapeutic utility via inhibition of Phosphodiesterase IV esterase and/or Tumor Necrosis factor activity.

PCT/US01/16494 discloses heterocycle carboxamides as antiviral agents.

Despite the above teachings, there still exists a need in the art for compounds that have enhanced oral bioavailability and improved selectivity for the viral targets.

SUMMARY OF THE INVENTION

The present invention provides a compound of formula I,

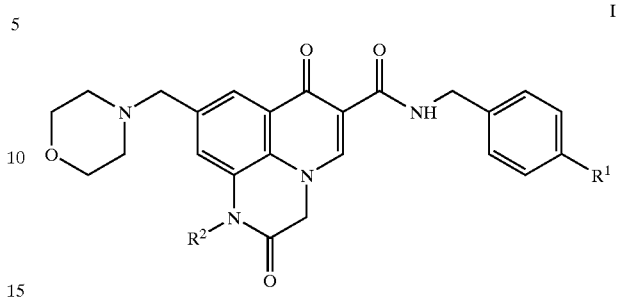

I or a pharmaceutically acceptable salt thereof wherein:

$R^1$ is F, Cl, Br, CN or $NO_2$;

$R^2$ is $C_{1-6}$alkyl, optionally substituted by one to three $OR^3$, $NR^3R^3$, aryl or het;

$R^3$ is hydrogen or $C_{1-4}$ alkyl;

het is morpholinyl, piperidinyl, piperazinyl, pyrrolidinyl, pyridyl, imidazolyl, azetidyl, tetrahydrofuranyl or imidazolidinyl; and aryl is a phenyl or pyridyl radical, attached via a carbon atom, optionally substituted by one to three halogen, $OR^3$ or $NR^3R^3$.

The present invention further provides a pharmaceutical composition comprising a compound of formula I, or a pharmaceutically acceptable salt thereof, and a pharmaceutically acceptable carrier (the composition preferably comprises an effective antiviral amount of the compound or salt).

The present invention further provides a method of treating or preventing a herpesviral infection, comprising administering to a mammal in need of such treatment, a compound of formula I or a pharmaceutically acceptable salt thereof.

The present invention further provides a method of treating or preventing a herpesviral infection comprising administering orally, parenterally, topically, rectally, nasally, sublingually or transdermally an effective amount of a compound of formula I.

The present invention further provides a composition and method for the treatment of herpesviral infections comprising the step of administering a composition comprising a pharmaceutically effective amount of the compound of formula I and at least one other antiviral agent.

The present invention further provides a compound of formula I or a pharmaceutically acceptable salt thereof for use in medical treatment.

The present invention further provides the use of a compound of formula I or a pharmaceutically acceptable salt thereof to prepare a medicament for treating or preventing a herpesviral infection in a mammal.

The present invention further provides a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

The following definitions are used, unless otherwise described. Alkyl denotes both straight and branched groups; but reference to an individual radical such as "propyl"

embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-4})$alkyl refers to alkyl of one to four carbon atoms, inclusive, or methyl, ethyl, propyl, isopropyl and butyl, straight and branched forms thereof.

Mammal denotes human and animals. Animals specifically refers to food animals or companion animals.

Compounds of the invention may have one or more chiral centers and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specifically, $R^1$ is chloro.

Specifically, $R^2$ is methyl.

Specifically, $R^2$ is $C_{1-4}$ alkyl, optionally substituted by OH or $NH_2$.

Specifically, $R^2$ is $C_{1-4}$ alkyl optionally substituted by $OC_{1-3}$ alkyl Specifically, $R^2$ is $C_{1-4}$ alkyl, optionally substituted by morpholinyl, piperidinyl, piperazinyl, or pyrrolidinyl.

Examples of the compounds of the present invention are:

a). N-(4-chlorobenzyl)-1-methyl-9-(morpholin-4-ylmethyl)-2,7-dioxo-2,3-dihydro-1H,7H-pyrido[1,2,3-de]quinoxaline-6-carboxamide, b). N-(4-chlorobenzyl)-1-ethyl-9-(morpholin-4-ylmethyl)-2,7-dioxo-2,3-dihydro-1H,7H-pyrido[1,2,3-de]quinoxaline-6-carboxamide, c). N-(4-chlorobenzyl)-1-(2-hydroxyethyl)-9-(morpholin-4-ylmethyl)-2,7-dioxo-2,3-dihydro-1H,7H-pyrido[1,2,3-de]quinoxaline-6-carboxamide, d). N-(4-chlorobenzyl)-9-(morpholin-4-ylmethyl)-2,7-dioxo-1-(2-phenylethyl)-2,3-dihydro-1H,7H-pyrido[1,2,3-de]quinoxaline-6-carboxamide, e). N-(4-chlorobenzyl)-1-(2-hydroxy-2-phenylethyl)-9-(morpholin-4-ylmethyl)-2,7-dioxo-2,3-dihydro-1H,7H-pyrido[1,2,3-de]quinoxaline-6-carboxamide, f). N-(4-chlorobenzyl)-1-(2,3-dihydroxypropyl)-9-(morpholin-4-ylmethyl)-2,7-dioxo-2,3-dihydro-1H,7H-pyrido[1,2,3-de]quinoxaline-6-carboxamide, g). N-(4-chlorobenzyl)-1-(2-methoxyethyl)-9-(morpholin-4-ylmethyl)-2,7-dioxo-2,3-dihydro-1H,7H-pyrido[1,2,3-de]quinoxaline-6-carboxamide, h). N-(4-chlorobenzyl)-1-(3-hydroxypropyl)-9-(morpholin-4-ylmethyl)-2,7-dioxo-2,3-dihydro-1H,7H-pyrido[1,2,3-de]quinoxaline-6-carboxamide, i). N-(4-fluorobenzyl)-1-methyl-9-(morpholin-4-ylmethyl)-2,7-dioxo-2,3-dihydro-1H,7H-pyrido[1,2,3-de]quinoxaline-6-carboxamide, or j). N-(4-chlorobenzyl)-9-(morpholin-4-ylmethyl)-2,7-dioxo-1-(tetrahydrofuran-2-ylmethyl)-2,3-dihydro-1H,7H-pyrido[1,2,3-de]quinoxaline-6-carboxamide.

Chart A describes the preparation of the compounds of formula I of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry.

CHART A

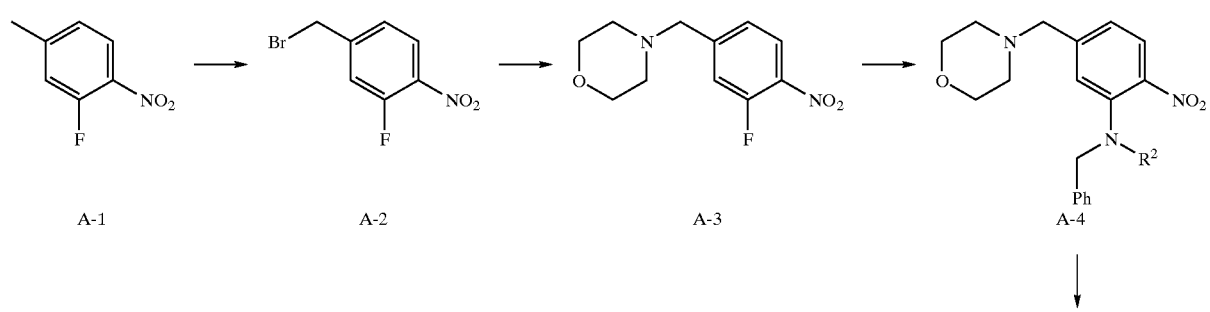

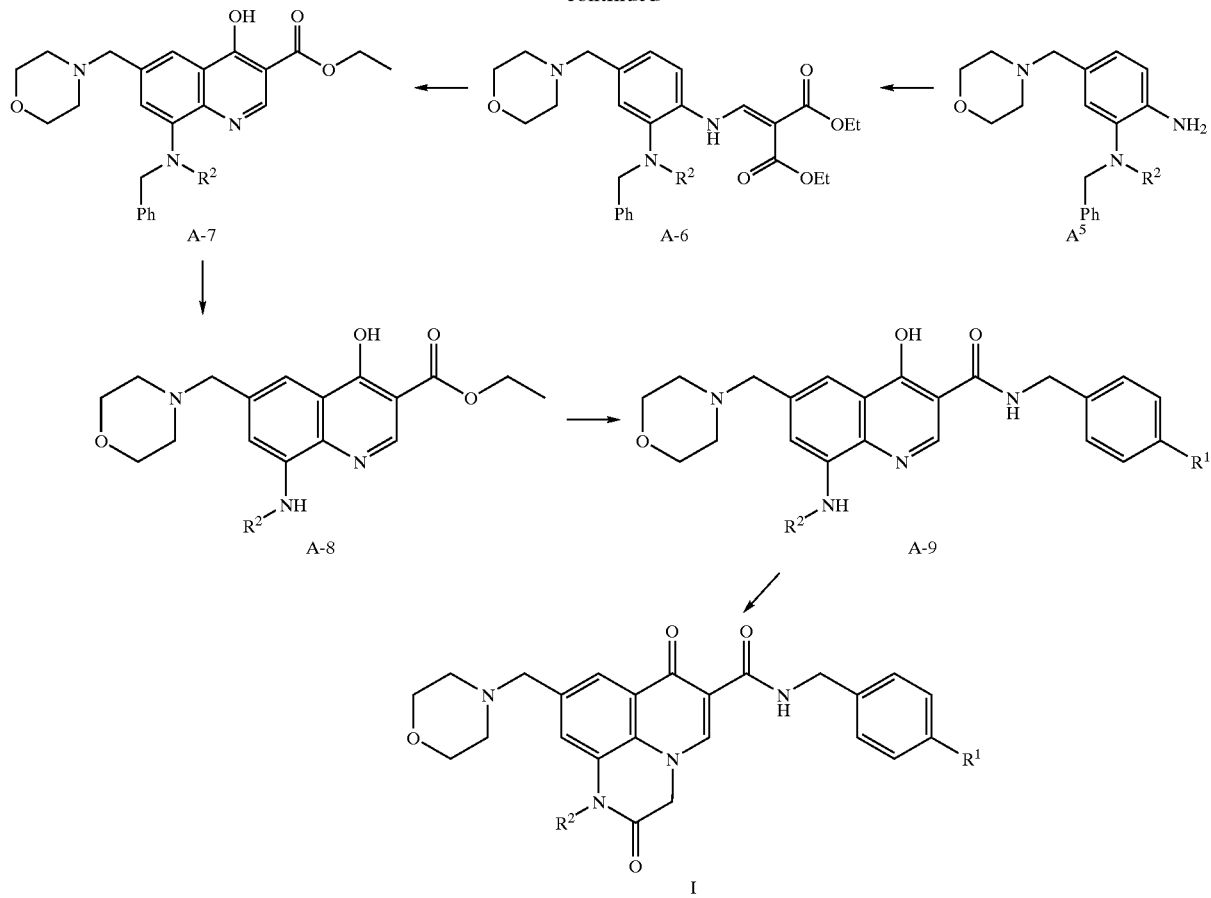

As shown in Chart A, the starting material is brominated to give compound 2 which is reacted with morpholine to give 4-(3-fluoro-4-nitrobenzyl)morpholine. This intermediate is reacted with an N-benzylalkylamine to give compound 4 wherein $R^2$ is a lower alkyl group. The nitro group is then reduced by catalytic hydrogenation to give compound 5. Reacting compound 5 with diethyl ethoxymethylenemalonate provides compound 6, which is heated in a mixture of phenyl ether and biphenyl at higher than 200° C. to give compound 7. Catalytic hydrogenation of this compound affords compound 8 which is reacted with a substituted ($R^1$ as defined) benzylamine to give compound 9. Reaction of compound 9 with bromoacetic anhydride provide a compound of formula I.

CHART B

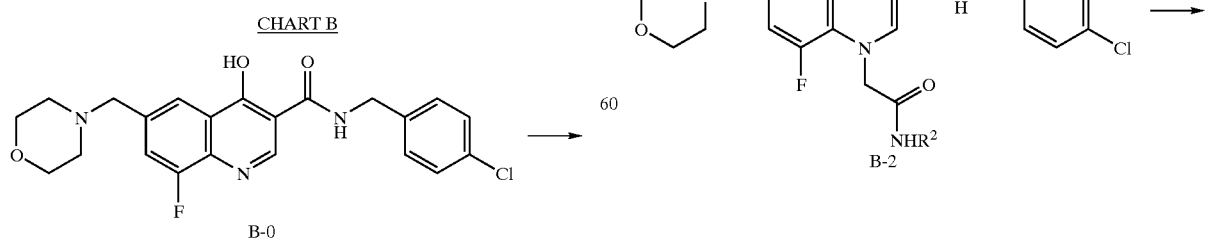

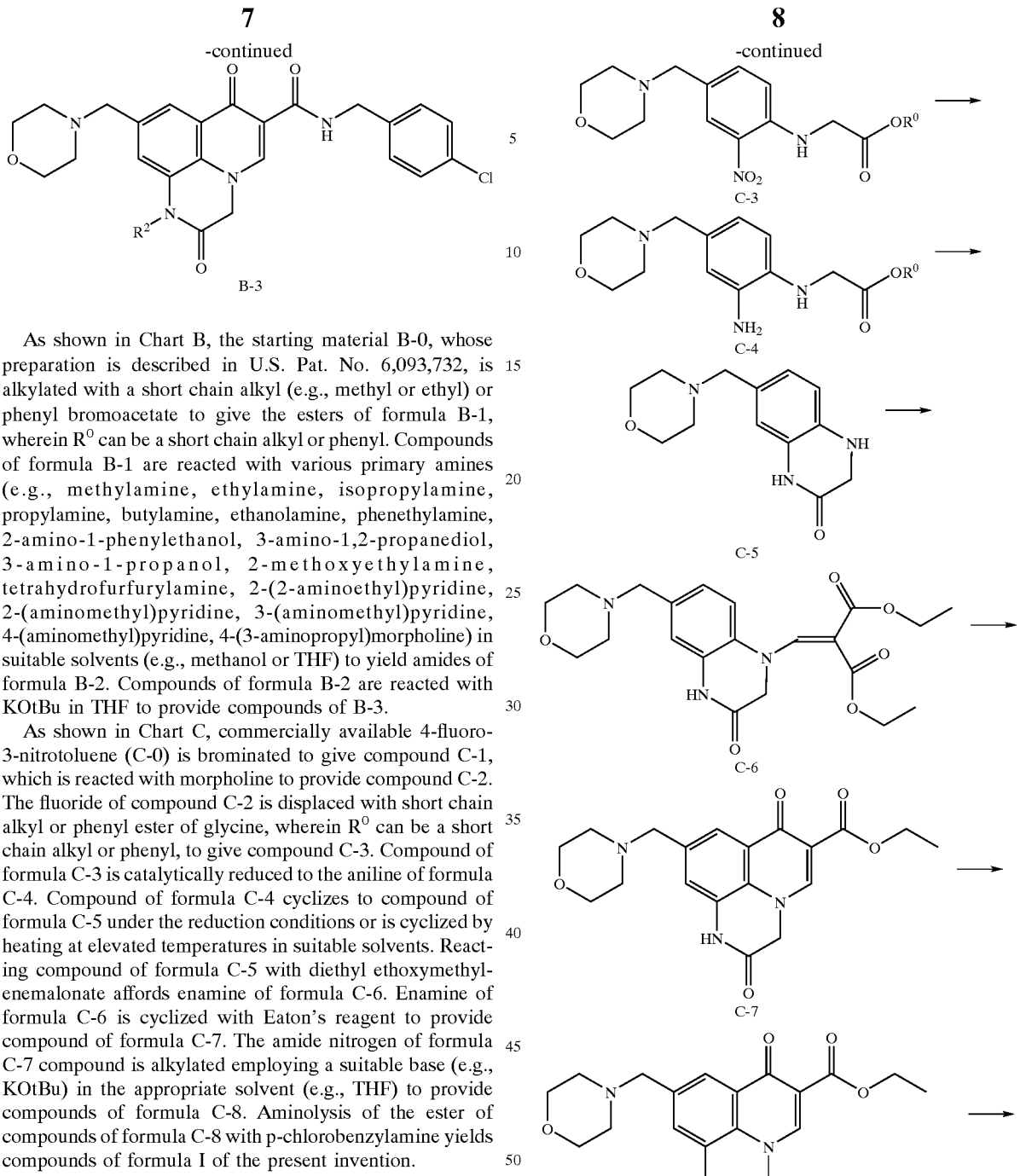

As shown in Chart B, the starting material B-0, whose preparation is described in U.S. Pat. No. 6,093,732, is alkylated with a short chain alkyl (e.g., methyl or ethyl) or phenyl bromoacetate to give the esters of formula B-1, wherein $R^0$ can be a short chain alkyl or phenyl. Compounds of formula B-1 are reacted with various primary amines (e.g., methylamine, ethylamine, isopropylamine, propylamine, butylamine, ethanolamine, phenethylamine, 2-amino-1-phenylethanol, 3-amino-1,2-propanediol, 3-amino-1-propanol, 2-methoxyethylamine, tetrahydrofurfurylamine, 2-(2-aminoethyl)pyridine, 2-(aminomethyl)pyridine, 3-(aminomethyl)pyridine, 4-(aminomethyl)pyridine, 4-(3-aminopropyl)morpholine) in suitable solvents (e.g., methanol or THF) to yield amides of formula B-2. Compounds of formula B-2 are reacted with KOtBu in THF to provide compounds of B-3.

As shown in Chart C, commercially available 4-fluoro-3-nitrotoluene (C-0) is brominated to give compound C-1, which is reacted with morpholine to provide compound C-2. The fluoride of compound C-2 is displaced with short chain alkyl or phenyl ester of glycine, wherein $R^0$ can be a short chain alkyl or phenyl, to give compound C-3. Compound of formula C-3 is catalytically reduced to the aniline of formula C-4. Compound of formula C-4 cyclizes to compound of formula C-5 under the reduction conditions or is cyclized by heating at elevated temperatures in suitable solvents. Reacting compound of formula C-5 with diethyl ethoxymethyl-enemalonate affords enamine of formula C-6. Enamine of formula C-6 is cyclized with Eaton's reagent to provide compound of formula C-7. The amide nitrogen of formula C-7 compound is alkylated employing a suitable base (e.g., KOtBu) in the appropriate solvent (e.g., THF) to provide compounds of formula C-8. Aminolysis of the ester of compounds of formula C-8 with p-chlorobenzylamine yields compounds of formula I of the present invention.

CHART C

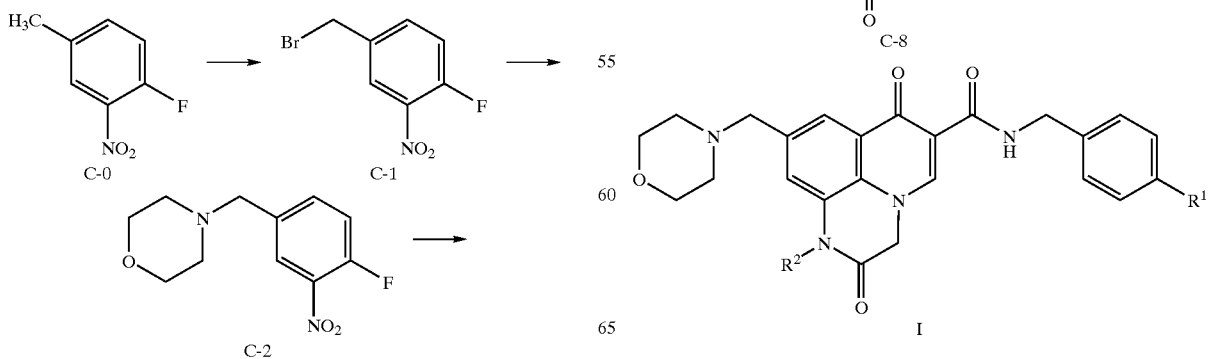

As shown in Chart D, commercially available 3-fluoro-4-nitrotoluene (D-0) is brominated to give compound D-1, which is reacted with morpholine to provide compound D-2. Compound D-2 is displaced with an amine (e.g., methylamine) to give compounds of formula D-3. Compounds of formula D-3 are catalytically reduced with hydrogen gas over 5% platinum on carbon and acylated with chloroacetic anhydride in THF to give compounds of formula D-4. Treatment with aqueous hydroxide (e.g., NaOH) in THF converts compounds of formula DA to the free base and affects cyclization to compounds of formula D-5. Reacting compounds of formula D-5 with diethyl ethoxymethyl-enemalonate affords enamines of formula D-6. Compounds of formula D-6 are cyclized with Eaton's reagent to provide compounds of formula D-7. Aminolysis of the ester of compounds of formula D-7 with a benzylamine (e.g., p-chlorbenzylamine) yields compounds of formula I of the present invention.

CHART D

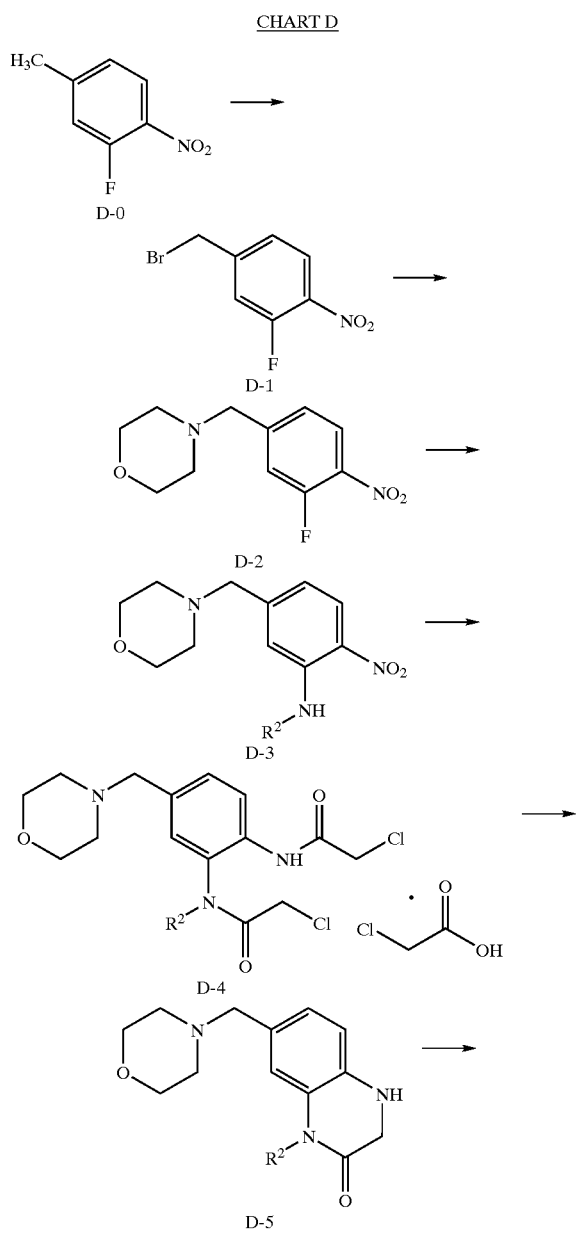

-continued

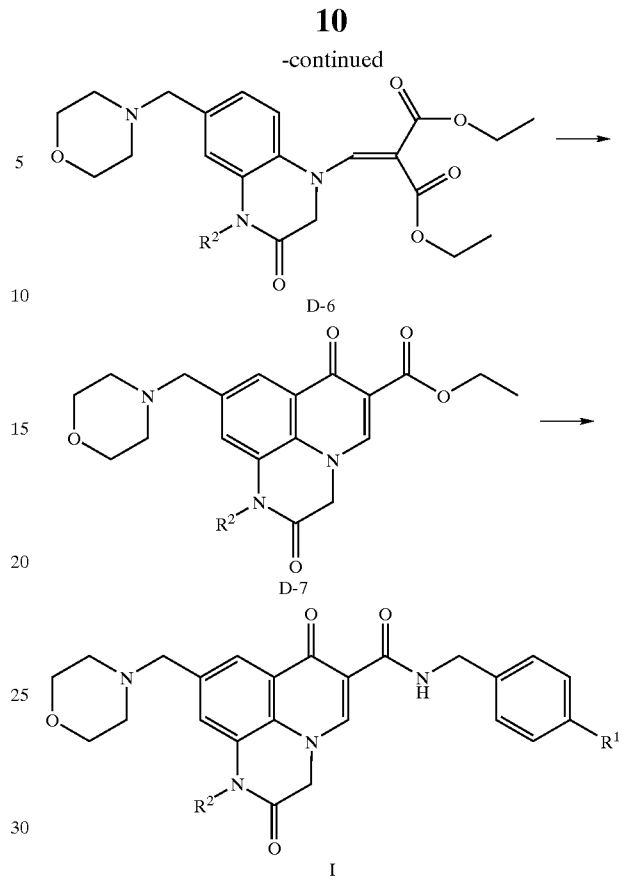

Pharmaceutical Salts

The compound of formula I may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a compound of the invention with a suitable acid affording a physiologically acceptable anion.

Routes of Administration

In therapeutic use for treating, or combating, viral infections in a mammal (i.e. human and animals) a compound of the present invention, its pharmaceutical compositions and other antiviral agents can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injection, bolus injection or continuous infusion. Formulations for parenteral administration may be presented in unit dosage form. e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxpropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevention of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, an antiviral effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the viral infection being treated. In average, the effective amount of active component is about 200/mg to 800/mg and preferable 600/mg per day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

The compounds of the present invention and pharmaceutically acceptable salts thereof are useful as antiviral agents. Thus, these compounds are useful to combat viral infections in mammals. Specifically, these compounds have anti-viral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

The compounds of the present invention may also useful for the treatment of several cardiovascular diseases such as atherosclerosis and restenosis. These diseases have been connected with inflammation of coronary vessel walls resulting from infection or reactivation of herpesviruses.

The compounds of the present invention may also be useful for the treatment of herpesvirus infections in animals, for example, illnesses caused by bovine herpesvirus 1–5 (BHV), ovine herpesvirus 1 and 2, Canine herpesvirus 1, equine herpesvirus 1–8 (EHV), feline herpesvirus 1 (FHV), and pseudorabies virus (PRV).

Without further elaboration, it is believed that one skilled in the art can, using the preceding description, practice the present invention to its fullest extent. The foregoing detailed description is given for clearness of understanding only, and no unnecessary limitations should be understood therefrom, as modifications within the scope of the invention may become apparent to those skilled in the art.

EXAMPLES

Example 1

Preparation of N-(4-Chlorobenzyl)-1-methyl-9-(morpholin-4-ylmethyl)-2,7-dioxo-2,3-dihydro-1H,7H-pyrido[1,2,3-de]quinoxaline-6-carboxamide.

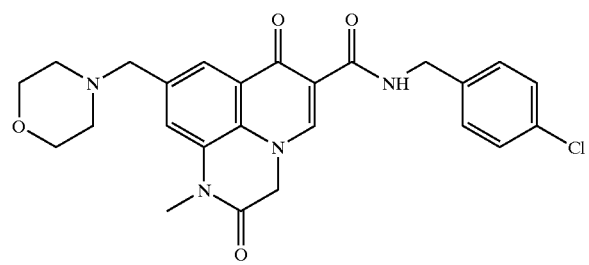

Procedure A

Step 1: Preparation of 4-(bromomethyl)-2-fluoronitrobenzene

A stirred suspension of N-bromosuccinimide (NBS, 24.0 g, 136 mmol) and 3-fluoro4-nitrotoluene (12.1 g, 78 mmol) in 1,2-dichoroethane (DCE, 250 mL) is irradiated with a 650 watt sunlamp for 1 h. For the first 60 min, the temperature of the solution is maintained between 0 and 25 ° C. with external cooling; most of the NBS dissolves during this time. The cooling bath is then removed and irradiation is continued for 15 min so as to complete the reaction. The DCE is evaporated under reduced pressure and the residual oil is partitioned between ether (150 mL) and water (100 mL). The product is chromatographed on silica gel to give a first fraction of 19.9 g of material, a 3:2 mixture of the title compound and 4-(bromomethyl)-2-fluoro-1-nitrobenzene. A second fraction of the pure title compound (3.4 g) is obtained, and this is recrystallized from ether/hexane.

Physical characteristics: mp 46–49° C. Anal. Calcd for $C_7H_5BrFNO_2$: C, 35.93; H, 2.15; N, 5.99. Found: C, 35.83; H, 1.95; N, 5.81. $^1$H NMR (CDCl$_3$) δ4.48, 7.28–7.38, and 8.08.

Step 2: Preparation of 4-(3-fluoro4-nitrobenzyl) morpholine

The first fraction from Step 1 (19.9 g) is dissolved in THF (500 mL), stirred, and morpholine (10 mL) is added. After 1 h, the solution is filtered to remove morpholine hydrochloride and the THF is evaporated. The residual oil is partitioned between ether (250 mL) and saturated sodium bicarbonate solution (100 mL). The ether phase is washed with water, evaporated, and the residual oil is chromatographed on silica gel with chloroform as the initial eluant. The first compounds to elute from the column are 4-(bromomethyl)-2-fluoro-1-nitrobenzene and 4-[3-(dibromomethyl)-4-nitrophenyl]morpholine. Continued elution of the column gives 11.4 g of the title compound. A sample was crystallized from ethyl acetate/hexane for analysis.

Physical characteristics: mp 76–78° C. Anal. Calcd for $C_{11}H_{13}FN_2O_3$: C, 55.00; H, 5.45; N, 11.66. Found: C, 55.10; H, 5.47; N, 11.66. $^1$H NMR (CDCl$_3$) δ2.48, 3.57, 3.75, 7.29, 7.36, and 8.04.

Step 3: Preparation of N-benzyl-N-methyl-5-(4-morpholinylmethyl)-2-nitroaniline A mixture of N-benzylmethylamine (3.6 g, 30 mmol) and 4-(3-fluoro-4-nitrobenzyl)morpholine (2.4 g, 10 mmol) in acetonitrile (3.0 mL) is heated under reflux for 30 min and the solvent is then removed under reduced pressure. The residual oil is partitioned between ethyl acetate (70 mL) and sodium hydroxide solution (10 mL of 1 N) and the ethyl acetate phase is separated and washed twice with water (5 mL). The ethyl acetate is removed and the crude product is applied to a silica gel column. The column is eluted with 50% ethyl acetate/hexane to give 3.3 g of the title compound as an oil.

Physical characteristics: $^1$H NMR (CDCl$_3$) δ2.38, 2.82, 3.45, 3.66, 4.43, 6.86, 7.05, 7.25–7.37, and 7.75.

Step 4: Preparation of $N^2$-benzyl-$N^2$-methyl-4-(4-morpholinylmethyl)-1,2-benzenediamine A mixture of N-benzyl-N-methyl-5-(4-morpholinylmethyl)-2-nitroaniline (3.3 g, 9.7 mmol) and 10% palladium charcoal (0.25 g) in ethyl acetate (100 mL) is hydrogenated (50 psi initial hydrogen pressure) until HPLC shows that reaction is complete (40 min). The solvent is evaporated to give 3.1 g of the title compound as an oil.

Physical characteristics: $^1$H NMR (CDCl$_3$) δ2.40, 2.62, 3.41, 3.72, 4.07, 6.73, 7.89, 6.96, and 7.23–7.38.

Step 5: Preparation of Diethyl 2-{[2-[benzyl (methyl)amino]-4-(4-morpholinylmethyl)anilino] methylene}malonate A mixture of $N^2$-benzyl-$N^2$-methyl-4-(4-morpholinylmethyl)-1,2-benzenediamine (3.1 g, 10 mmol) and diethyl ethoxymethylenemalonate (4.2 g, 20 mmol) is heated at 120° C. until HPLC shows that the reaction is complete (20 min). The product is applied in 10% ethyl acetate/hexane to a silica gel column which is eluted with 20% ethyl acetate/hexane to remove excess diethyl ethoxymethylenemalonate and then with 50% ethyl acetate/hexane to elute 3.7 g of the title compound as an oil.

Physical characteristics: $^1$H NMR (CDCl$_3$) δ1.36, 1.41, 2.38, 2.67, 3.44, 3.70, 4.09, 4.30, 4.35, 7.07–7.38, 8.58, and 11.5.

Step 6: Preparation of Ethyl 8-[benzyl(methyl) amino]-4-hydroxy-6-(4-morpholinylmethyl)-3-quinolinecarboxylate Diethyl 2-{[2-[benzyl(methyl)amino]-4-(4-morpholinylmethyl)anilino]-methylene}malonate (3.7 g, 7.7 mmol) is stirred in a mixture of phenyl ether (9 g) and biphenyl (3 g) at 260° C. A slow stream of nitrogen is passed through the solution to remove volatile materials produced in the reaction. The reaction is stopped as soon as HPLC shows that conversion of the starting material to product is complete (60 min). After cooling, the reaction mixture is applied in ethyl acetate to a silica gel column which is eluted with ethyl acetate (400 mL) to remove phenyl ether and biphenyl. The column is then eluted with 5–10% methanol/chloroform and the product obtained is recrystallized from ethyl acetate/hexane (3:1, 15 mL) to give 1.70 g of the title compound.

Physical characteristics: mp 151–153° C. Anal. Calcd for $C_{25}H_{29}N_3O_4$: C, 68.94; H, 6.71; N, 9.65. Found: C, 68.91; H, 6.74; N, 9.56. $^1$H NMR [(CD$_3$)$_2$SO] δ1.28, 2.23, 2.70, 3.39, 3.52, 4.21, 4.24, 7.15–7.25, 7.34, 7.74, 8.44, and 11.5.

Step 7: Preparation of Ethyl 4-hydroxy-8-(methylamino)-6-(4-morpholinylmethyl)-3-quinolinecarboxylate A mixture of ethyl 8-[benzyl(methyl)amino]4-hydroxy-6-(4-morpholinylmethyl)-3-quinolinecarboxylate (500 mg, 1.15 mmol), 10% palladium charcoal (0.25 g) in ethanol (100 mL) is hydrogenated (50 psi initial hydrogen pressure) until HPLC shows that all the starting material has been reduced (2.5 h). The solution is filtered, the solvent removed, and the residual oil is applied in chloroform to a silica gel column which is eluted with 5–10% methanol/chloroform. After elution of a small amount of ethyl 4-hydroxy-8-(methylamino)-6-methyl-3-quinolinecarboxylate, the title compound (280 mg) is obtained.

Physical characteristics: $^1$H NMR (CDCl$_3$ δ1.50, 2.52, 3.06, 3.62, 3.70, 4.50, 6.07, 6.82, 7.43, 8.93, and 12.2.

Step 8: Preparation of N-(4-Chlorobenzyl)-4-hydroxy-8-(methylamino)-6-(4-morpholinylmethyl)-3-quinolinecarboxamide A mixture of ethyl 4-hydroxy-8-(methylamino)-6-(4-morpholinylmethyl)-3-quinolinecarboxylate (280 mg) and 4-chlorobenzylamine (1.5 mL) is heated under nitrogen at 200° C. for 30 min. The bulk of the 4-chlorobenzylamine is removed under reduced pressure, and the product is purified by chromatography on silica gel to give 169 mg of the title compound as an oil.

Physical characteristics: $^1$H NMR (CDCl$_3$ δ2.47, 2.86, 3.56, 3.72, 4.58, 5.2, 6.89, 7.25–7.35, 7.65, 8.45, and 11.2.

Step 9: Preparation of N-(4-Chlorobenzyl)-1-methyl-9-(morpholin-4-ylmethyl)-2,7-dioxo-2,3-dihydro-1H,7H-pyrido[1,2,3-de]quinoxaline-6-carboxamide A solution of bromoacetic anhydride (1.03 g, 4 mmol) in THF (3.0 mL) is added over 30 min to a stirred solution of N-(4-chlorobenzyl)-4-hydroxy-8-(methylamino)-6-(4-morpholinylmethyl)-3-quinolinecarboxamide (308 mg of a 1:1 mixture of compound 9 and 4-chlorobenzylamine), triethylamine (500 mg, 5 mmol) in THF (7.0 mL). After 5 h, methanol (20 mL) and triethylamine (300 mg) are added, and the solution is stirred at room temperature overnight. The solution is evaporated, dissolved in chloroform/methanol, and is applied in chloroform to a silica gel column which is eluted with chloroform and then with 5–10% methanol/chloroform to give the title compound (98 mg) which is precipitated from acetonitrile.

Physical characteristics: $^1$H NMR (CDCl$_3$) δ2.48, 3.56, 3.64, 3.73, 4.66, 5.01, 7.31, 7.42, 8.04, 8.68, and 10.3.

Procedure B

Step 1: Preparation of 4-(3-fluoro-4-nitrobenzyl)morpholine

A slurry of N-bromosuccinimide (167 g), 3-fluoro-4-nitrotoluene (135 g), 2,2'-azoisobutyronitrile (17.1 g) and 1,2-dichloroethane (1120 g) is stirred at 60° C. for 2 hours and then at 80° C. for 30 min. The reaction mixture is cooled to 23° C. and water (300 ml) is added. The phases are separated and the aqueous is washed with methylene chloride (300 ml). The combined organics are concentrated. Methanol (400 ml) is added and the mixture is cooled to −5° C. Morpholine (218 g) is added slowly while maintaining −5 to 14° C. While maintaining 6 to 14° C., 37% hydrochloric acid (113 ml) is added to adjust the observed pH from 8 to 6. Water (650 ml) and toluene (650 ml) are added and the mixture is warmed to 25° C. The phases are separated and the aqueous is washed with toluene (2×600 ml). To the combined organics is added water (400 ml) followed by 37% hydrochloric acid (53 g). The phases are separated and the organic is washed with water (500 ml). At room temperature, the pH of the combined aqueous is slowly adjusted to pH of 9 with 50% aqueous sodium hydroxide to yield a yellow slurry. The precipitate is collected by filtration, washed with water (200 ml) and is dried in a nitrogen stream to afford a yellow solid (104 g). Physical characteristics: $^1$H NMR (400 MHz, CDCl$_3$) δ2.47, 3.56, 3.73, 7.27, 7.35, 8.02; $^{13}$C NMR (100 MHz, CDCl$_3$) δ53.55, 61.99, 66.83, 118.08, 124.33, 126.01, 148.10, 155.64; MS (EI) m/z 240; Anal. Found: C, 54.84; H, 5.47; N, 11.62.

Step 2: Preparation of N-methyl-5-(morpholin-4-ylmethyl)-2-nitroaniline

An aqueous solution of methylamine (40 wt %, 910 ml) at 30° C. is added to a 61° C. solution of 4-(3-fluoro-4-nitrobenzyl)morpholine (504 g) in DMSO (810 ml) followed by a DMSO rinse (150 ml) over ½ h. The mixture is allowed to reflux at 47 ° C. over 5 min then maintained at <51° C. by occasional ice bath cooling for remainder of the addition. The mixture is stirred at 50° C. for ¾ h and then water (2000 ml) is added. The mixture is cooled to 0° C. and the precipitate is collected by filtration, washed with water (1500 ml) and is dried in a nitrogen stream to give a bright orange solid (529 g). Physical characteristics: $^1$H NMR (400 MHz, DMSO-d$_6$) δ2.35, 2.93, 3.44, 3.56, 6.63, 6.64, 7.78, 8.15; $^{13}$C NMR (100 MHz, DMSO-d$_6$) δ29.95, 53.57, 62.27, 66.54, 113.69, 115.76, 126.49, 130.16, 146.27, 148.07.

Step 3: Preparation of 2-chloro-N-[2-[(chloroacetyl)amino]-5-(morpholin-4-ylmethyl)phenyl]-N-methylacetamide chloroacetic acid salt A slurry of N-methyl-5-(morpholin-4-ylmethyl)-2-nitroaniline (311 g) and 5% platinum on carbon (9.0 g) in THF (370 ml) at 14° C. is hydrogenated at 50 psi pressure with external cooling of the autoclave jacket over 1 hr. The procedure is repeated on an additional sample of N-methyl-5-(morpholin-4-ylmethyl)-2-nitroaniline (302). The hydrogenation mixtures are combined and the catalyst is removed by filtration on THF wet solka floc (16.7 g) in a nitrogen box and rinsed through with THF. The THF solution is cooled to 10° C. and a solution of chloroacetic anhydride (90% technical grade, 1240g) in THF (1800 ml) at 30° C. is added over ½ h while maintaining 8–11° C. with occasional dry ice/acetone bath cooling. After the addition is complete, a thick, stirrable slurry is formed. After ½ h, the chloroacetic anhydride solution is rinsed in with MTBE (1900 ml) over 15 min while maintaining 10° C. The resultant thinner slurry is cooled to −15° C. and the precipitate collected by filtration, washed with MTBE (2500 ml) and dried in a nitrogen stream to give a white solid (1220 g). Physical characteristics: $^1$H NMR (400 MHz, DMSO-d$_6$) δ2.43, 2.49, 3.05, 3.53, 3.58, 3.83, 3.98, 4.24, 4.30, 7.35, 7.37, 7.73, 9.85; $^{13}$C NMR (100 MHz, DMSO-d$_6$) δ36.26, 41.63, 42.43, 43.11, 52.83, 60.97, 65.91, 125.29, 129.42, 129.73, 132.98, 134.73, 135.59, 165.60, 165.66, 168.62.

Step 4: Preparation of diethyl 2-{[4-methyl-6-(morpholin-4-ylmethyl)-3-oxo-3,4-dihydroquinoxalin-1(2H)-yl]methylene}malonate A solution of 2-chloro-N-[2-[(chloroacetyl)amino]-5-(morpholin-4-ylmethyl)phenyl]-N-methylacetamide chloroacetic acid salt (792 g) in THF (2000 ml) and water (1600 ml) is added aqueous sodium hydroxide (532 g, 50 wt %) while maintaining 13–17° C. via occasional cooling with a dry ice/acetone bath. After 20 min, a solution of ammonium chloride (89 g) in water (400 ml) is added followed by toluene (2000 ml). The phases are separated and the organic is washed with water (100 ml). The combined aqueous are back extracted with a mixture of THF (1000 ml) and toluene (1300 ml). The THF/toluene back extract is washed with water (100 ml). The combined aqueous is back extracted with a mixture of THF (1000 ml) and toluene (1300 ml). The THF/ toluene back extract is washed with water (100 ml). The combined aqueous is back extracted with a mixture of THF (1000 ml) and toluene (1300 ml). The combined organics are concentrated in vacuo. Isopar-H (5.35 liter) and diethyl ethoxymethylenemalonate (394 g) are added and the mixture is warmed to 123° C. with distillation of a small amount of solvent and stirred at 122 to 125° C. for 3 h. The resultant solution is slowly cooled to −2° C. over /2 h to give a slurry. The precipitate is collected by filtration, washed with branched octanes (2 liter) and dried in a nitrogen stream to give a light yellow solid (573 g). Physical characteristics: $^1$H NMR (400 MHz, CDCl$_3$) δ1.30, 1.35, 2.45, 3.41, 3.50, 3.72, 4.15, 4.23, 4.30, 6.99, 7.07, 7.75; $^{13}$C NMR (100 MHz, CDCl$_3$) δ14.14, 14.26, 29.01, 52.09, 53.57, 60.70, 61.26, 62.77, 66.89, 102.75, 115.50, 119.42, 124.45, 129.12, 131.42, 136.17, 146.18, 164.25, 165.79, 166.24; Anal. Found: C, 61.16; H, 6.91; N, 9.72.

Step 5: Preparation of ethyl 1-methyl-9-(morpholin-4-ylmethyl)-2,7-dioxo-2,3-dihydro-1H,7H-pyrido[1,2,3-de]quinoxaline-6-carboxylate Diethyl 2-{[4-methyl-6-(morpholin-4-ylmethyl)-3-oxo-3,4-dihydroquinoxalin-1(2H)-yl]methylene}malonate (915 g, 2.20 mol) is added to Eaton's reagent (4.05 kg, 7.7 wt % phosphorus pentoxide dimer in methanesulfonic acid). The resulting dark red mixture is heated to 90° C. After 2 h, the reaction is cooled to less than 30° C. and poured into 9 kg of ice. A solution of 50% NaOH (3.9 kg) in water (3.8 liter) is added while maintaining less than 35° C. until the pH is 10. Methylene chloride (4 liter) is added and the phases separated. The aqueous is washed with methylene chloride (3×4 liter) and the combined organics are concentrated in vacuo to 4.5 liter total volume. Acetonitrile (4.5 liter) is added and the mixture concentrated to 4.5 liter total volume. Acetonitrile (1.8 liter) is added and the mixture concentrated to 4.5 liter total volume. The resultant slurry is cooled to 0° C. and the precipitate collected by filtration, washed with 2×1 liter of 0° C. acetonitrile and dried in a vacuum oven at 50° C. overnight to give a white solid (756 g). Physical characteristics: $^1$H NMR (400 MHz, DMSO-d$_6$) δ1.27, 2.38, 3.36, 3.59, 4.21, 5.08, 7.33, 7.73, 8.48; $^{13}$C NMR (DMSO-d$_6$) δ172.2. 164.2, 161.6, 146.8, 135.4, 131.0, 127.3, 126.4, 119.2, 117.3, 111.3, 66.2, 61.9. 59.9, 53.1, 28.6, 14.3.

Step 6: Preparation of N-(4-chlorobenzyl)-1-methyl-9-(morpholin-4-ylmethyl)-2,7-dioxo-2,3-dihydro-1H, 7H-pyrido[ 1,2,3-de]quinoxaline-6-carboxamide.

Ethyl 1-methyl-9-(morpholin-4-ylmethyl)-2,7-dioxo-2,3-dihydro-1H, 7H-pyrido[1,2,3-de]quinoxaline-6-carboxylate (1200 g) is slurried in 4-chlorobenzylamine (1.33 kg) and ethylene glycol (3.6 liter). The mixture is carefully purged with 3 vacuum/nitrogen cycles and heated to 140° C. After 4 h, the resulting slurry is cooled to 80° C. and poured into ethanol (12 liter). The resulting slurry is cooled to less than 30° C. and the precipitate collected by vacuum filtration, washed with ethanol (2 liter) and dried in a vacuum oven at 60° C. to give a white solid (1213 g). A sample of this crude solid (400 g) is dissolved in methylene chloride (12 liter) and methanol (1.3 liter) at 35° C. The solution is clarified and then concentrated via atmospheric distillation to a 10 liter total volume. Ethanol (4×1 liter) is added with atmospherically distilling to 10 liters after each addition. The mixture is further concentrated atmospherically to 7 liters and ethanol (1.5 l) is added. The mixture is further concentrated atmospherically to 5 liters and ethanol (1.5 l) is added. The resulting slurry is cooled to 5° C. and the precipitate collected by vacuum filtration, washed with 0° C. ethanol (2 liter) and dried in a vacuum oven at 60° C. to give a white solid (392 g). Physical characteristics: $^1$H NMR (400 MHz, DMSO-d$_6$) δ2.39, 3.31, 3.6, 4.41, 4.55, 5.20, 7.36, 7.83, 8.71, 10.3; $^{13}$C NMR (75 MHz, DMSO-d$_6$) δ174.9, 163.9, 161.6, 145.9, 138.6, 135.7, 131.4, 131.2, 129.2, 128.4, 126.7, 126.4, 118.8, 117.4, 112.0, 66.3, 61.0, 53.1, 52.2, 41.5, 28.5; Anal. Found: C, 62.26%; H, 5.20%; N, 11.63%.

What is claimed is:

1. A compound of formula I

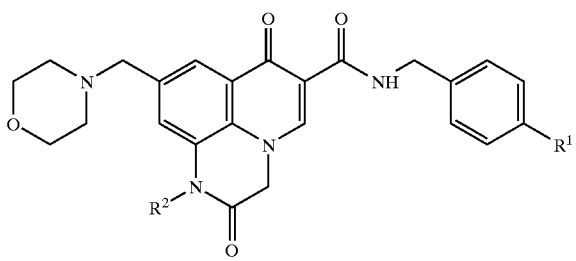

I or a pharmaceutically acceptable salt thereof
wherein $R^1$ is F, Cl, Br, CN or $NO_2$;
$R^2$ is $C_{1-6}$alkyl, optionally substituted by one to three $OR^3$, $NR^3R^3$, aryl or het;

$R^3$ is H or $C_{1-4}$alkyl;
het is morpholinyl, piperidinyl, piperazinyl, pyrrolidinyl, pyridyl, imidazolyl, azetidyl, tetrahydrofuranyl or imidazolidinyl;
and aryl is a phenyl or pyridyl radical, attached via a carbon atom, optionally substituted by one to three halogen, $OR^3$ or $NR^3R^3$.

2. A compound of claim 1 wherein $R^1$ is Cl.
3. A compound of claim 1 wherein R is methyl.
4. A compound of claim 1 wherein $R^2$ is $C_{1-4}$ alkyl, optionally substituted by OH or $NH_2$.
5. A compound of claim 2 or 3 wherein $R^2$ is $C_{1-4}$ alkyl, optionally substituted by OH or $NH_2$.
6. A compound of claim 1 wherein $R^2$ is $C_{1-4}$ alkyl, optionally substituted by $OC_{1-3}$ alkyl.
7. A compound of claim 2 or 3 wherein $R^2$ is $C_{1-4}$ alkyl, optionally substituted by $OC_{1-3}$ alkyl.
8. A compound of claim 1 wherein $R^2$ is $C_{1-4}$ alkyl, optionally substituted by morpholinyl, piperidinyl, piperazinyl, or pyrrolidinyl.
9. A compound of claim 2 or 3 wherein $R^2$ is $C_{1-4}$ alkyl, optionally substituted by morpholinyl, piperidinyl, piperazinyl, or pyrrolidinyl.
10. A compound of claim 1 which is
 a). N-(4-chlorobenzyl)-1-methyl-9-(morpholin-4-ylmethyl)-2,7-dioxo-2,3-dihydro-1H,7H-pyrido[1,2,3-de]quinoxaline-6-carboxamide,
 b). N-(4-chlorobenzyl)-1-ethyl-9-(morpholin-4-ylmethyl)-2,7-dioxo-2,3-dihydro-1H,7H-pyrido[1,2,3-de]quinoxaline-6-carboxamide,
 c). N-(4-chlorobenzyl)-1-(2-hydroxyethyl)-9-(morpholin-4-ylmethyl)-2,7-dioxo-2,3-dihydro-1H,7H-pyrido[1,2,3-de]quinoxaline-6-carboxamide,
 d). N-(4-chlorobenzyl)-9-(morpholin-4-ylmethyl)-2,7-dioxo-1-(2-phenylethyl)-2,3-dihydro-1H,7H-pyrido[1,2,3-de]quinoxaline-6-carboxamide,
 e). N-(4-chlorobenzyl)-1-(2-hydroxy-2-phenylethyl)-9-(morpholin-4-ylmethyl)-2,7-dioxo-2,3-dihydro-1H, 7H-pyrido[1,2,3-de]quinoxaline-6-carboxamide,
 f). N-(4-chlorobenzyl)-1-(2,3-dihydroxypropyl)-9-(morpholin-4-ylmethyl)-2,7-dioxo-2,3-dihydro-1H, 7H-pyrido[1,2,3-de]quinoxaline-6-carboxamide,
 g). N-(4-chlorobenzyl)-1-(2-methoxyethyl)-9-(morpholin-4-ylmethyl)-2,7-dioxo-2,3-dihydro-1H, 7H-pyrido[1,2,3-de]quinoxaline-6-carboxamide,
 h). N-(4-chlorobenzyl)-1-(3-hydroxypropyl)-9-(morpholin-4-ylmethyl)-2,7-dioxo-2,3-dihydro-1H, 7H-pyrido[1,2,3-de]quinoxaline-6-carboxamide,
 i). N-(4-fluorobenzyl)-1-methyl-9-(morpholin-4-ylmethyl)-2,7-dioxo-2,3-dihydro-1H,7H-pyrido[1,2,3-de]quinoxaline-6-carboxamide, or
 j). N-(4-chlorobenzyl )-9-(morpholin-4-ylmethyl)-2,7-dioxo-1-(tetrahydrofuran-2-ylmethyl)-2,3-dihydro-1H, 7H-pyrido[1,2,3-de]quinoxaline-6-carboxamide.
11. A compound of claim 1 which is N-(4-chlorobenzyl)-1-methyl-9-(morpholin-4-ylmethyl)-2,7-dioxo-2,3-dihydro-1H,7H-pyrido[1,2,3-de]quinoxaline-6-carboxamide.
12. A pharmaceutical composition comprising a compound of claim 1 and a pharmaceutically acceptable carrier.
13. A method of treating infections by herpesviruses which comprises administering to a mammal in need thereof a compound of claim 1.
14. The method of claim 13 wherein the mammal is a human.
15. The method of claim 13 wherein the mammal is an animal.

16. The method of claim 13 wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses 8.

17. The method of claim 13 wherein said herpesviruses is human cytomegalovirus.

18. The method of claim 13 wherein the compound of claim 1 is administered orally, parenterally or topically.

19. The method of claim 13 wherein the compound of claim 1 is in an amount of from about 0.1 to about 300 mg/kg of body weight.

20. The method of claim 13 wherein the compound of claim 1 is in an amount of from about 1 to about 30 mg/kg of body weight.

21. A method for inhibiting a viral DNA polymerase, comprising contacting the polymerase with an effective inhibitory amount of a compound of claim 1.

22. A method of treating atherosclerosis and restenosis comprising administering to a mammal in thereof a compound of claim 1.

23. The method of claim 22 wherein the compound of claim 1 is in an amount of from about 0.1 to about 300 mg/kg of body weight.

24. The method of claim 22 wherein the compound of claim 1 is in an amount of from about 1 to about 30 mg/kg of body weight.

25. The method of claim 13 wherein the compound of claim 1 is administered orally, parenterally or topically.

* * * * *